United States Patent
Neubauer et al.

(10) Patent No.: US 9,668,820 B2
(45) Date of Patent: Jun. 6, 2017

(54) INTEGRATED SURGICAL DEVICE COMBINING INSTRUMENT, TRACKING SYSTEM AND NAVIGATION SYSTEM

(75) Inventors: Timo Neubauer, Grasbrunn-Neukeferloh (DE); Ingmar Hook, Feldkirchen (DE)

(73) Assignee: Brainlab AG, Munich (DE)

( * ) Notice: Subject to any disclaimer, the term of this patent is extended or adjusted under 35 U.S.C. 154(b) by 64 days.

(21) Appl. No.: 13/389,564

(22) PCT Filed: Aug. 20, 2009

(86) PCT No.: PCT/EP2009/060760
§ 371 (c)(1),
(2), (4) Date: Feb. 8, 2012

(87) PCT Pub. No.: WO2011/020505
PCT Pub. Date: Feb. 24, 2011

(65) Prior Publication Data
US 2012/0143049 A1    Jun. 7, 2012

(51) Int. Cl.
*A61B 6/00* (2006.01)
*A61B 34/20* (2016.01)
(Continued)

(52) U.S. Cl.
CPC .............. *A61B 34/20* (2016.02); *A61B 90/98* (2016.02); *A61B 2017/00199* (2013.01);
(Continued)

(58) Field of Classification Search
CPC combination set(s) only.
See application file for complete search history.

(56) References Cited

U.S. PATENT DOCUMENTS

| 4,797,736 A * | 1/1989 | Kloots et al. ................. 348/370 |
| 5,389,101 A | 2/1995 | Heibrun et al. |

(Continued)

FOREIGN PATENT DOCUMENTS

| DE | 203 21 068 | 1/2006 |
| EP | 1 374 793 | 1/2004 |

(Continued)

OTHER PUBLICATIONS

International Search Report for International Application No. PCT/EP2009/060760 dated Apr. 14, 2010.
(Continued)

*Primary Examiner* — Katherine Fernandez
*Assistant Examiner* — Farshad Negarestan
(74) *Attorney, Agent, or Firm* — Tucker Ellis LLP

(57) ABSTRACT

The invention relates to an image guided surgery system comprising —a surgical instrument (14), —a tracking system for locating and tracking an object (20) in a surgical environment, the tracking system including a tracking sensor system, in particular a tracking camera system (16); and —a medical navigation system (15) processing tracking data from the tracking system and image data of the object (20), and outputting image data and navigational assistance on a display (13). The instrument (14), the tracking system including the sensor system (16) and the medical navigation system including the display are integrated in one single portable unit (10), or the instrument (14) and the medical navigation system including the display are integrated in one single portable unit (10), while at least the sensor system (34) of the tracking system is arranged at a location near a region of interest determined by the object (20) and the field of surgery.

15 Claims, 2 Drawing Sheets

Figure 1:
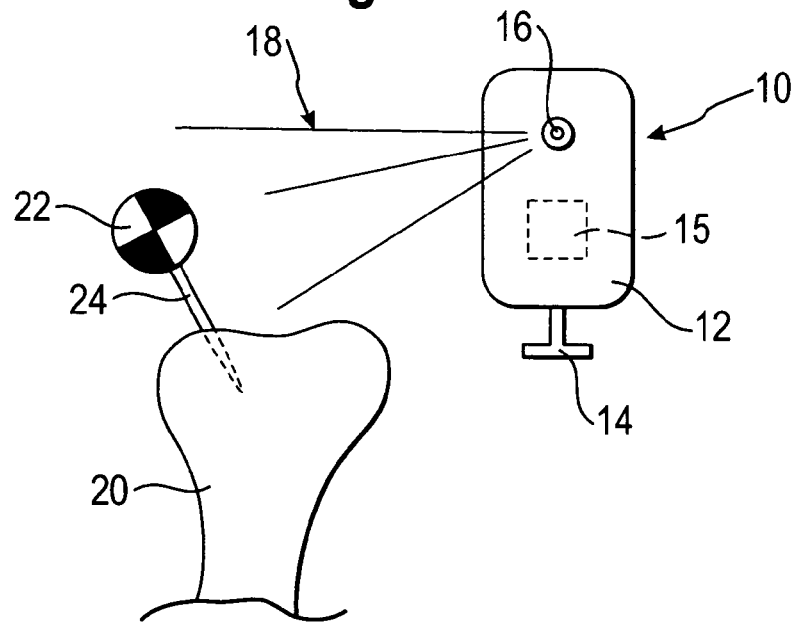

(51) Int. Cl.
*A61B 90/98* (2016.01)
*A61B 17/00* (2006.01)
*A61B 90/50* (2016.01)
*A61B 90/00* (2016.01)

(52) U.S. Cl.
CPC ............... *A61B 2034/2055* (2016.02); *A61B 2034/2068* (2016.02); *A61B 2034/2072* (2016.02); *A61B 2090/367* (2016.02); *A61B 2090/502* (2016.02)

(56) References Cited

U.S. PATENT DOCUMENTS

| | | | |
|---|---|---|---|
| 5,603,318 | A | 2/1997 | Heilbrun et al. |
| 6,221,007 | B1 * | 4/2001 | Green .................... 600/160 |
| 6,263,230 | B1 | 7/2001 | Haynor et al. |
| 6,434,416 | B1 | 8/2002 | Mizoguchi et al. |
| 6,978,167 | B2 | 12/2005 | Dekel et al. |
| 7,463,823 | B2 | 12/2008 | Birkenbach et al. |
| 7,577,474 | B2 | 8/2009 | Vilsmeier |
| 7,831,096 | B2 | 11/2010 | Williamson, Jr. |
| 2002/0095081 | A1 | 7/2002 | Vilsmeier |
| 2003/0210812 | A1 | 11/2003 | Khamene et al. |
| 2005/0288575 | A1 * | 12/2005 | de la Barrera et al. ....... 600/423 |
| 2007/0167708 | A1 | 7/2007 | Blumhofer et al. |
| 2007/0225550 | A1 * | 9/2007 | Gattani et al. ............... 600/101 |
| 2008/0009697 | A1 | 1/2008 | Haider et al. |
| 2008/0077158 | A1 | 3/2008 | Haider et al. |
| 2008/0132909 | A1 | 6/2008 | Jascob et al. |
| 2008/0188716 | A1 * | 8/2008 | Heckele et al. .............. 600/166 |

FOREIGN PATENT DOCUMENTS

| | | |
|---|---|---|
| WO | 00/21442 A1 | 4/2000 |
| WO | 2007/073551 A1 | 6/2007 |
| WO | 2007/113815 A2 | 10/2007 |
| WO | 2009097616 | 8/2009 |

OTHER PUBLICATIONS

Najwer et al., Improving Surgical Precision Application of Navigation System in Orthopedic Surgery, Acta of Bioengineering and Biomechanics, vol. 10, No. 4, 2008.

* cited by examiner

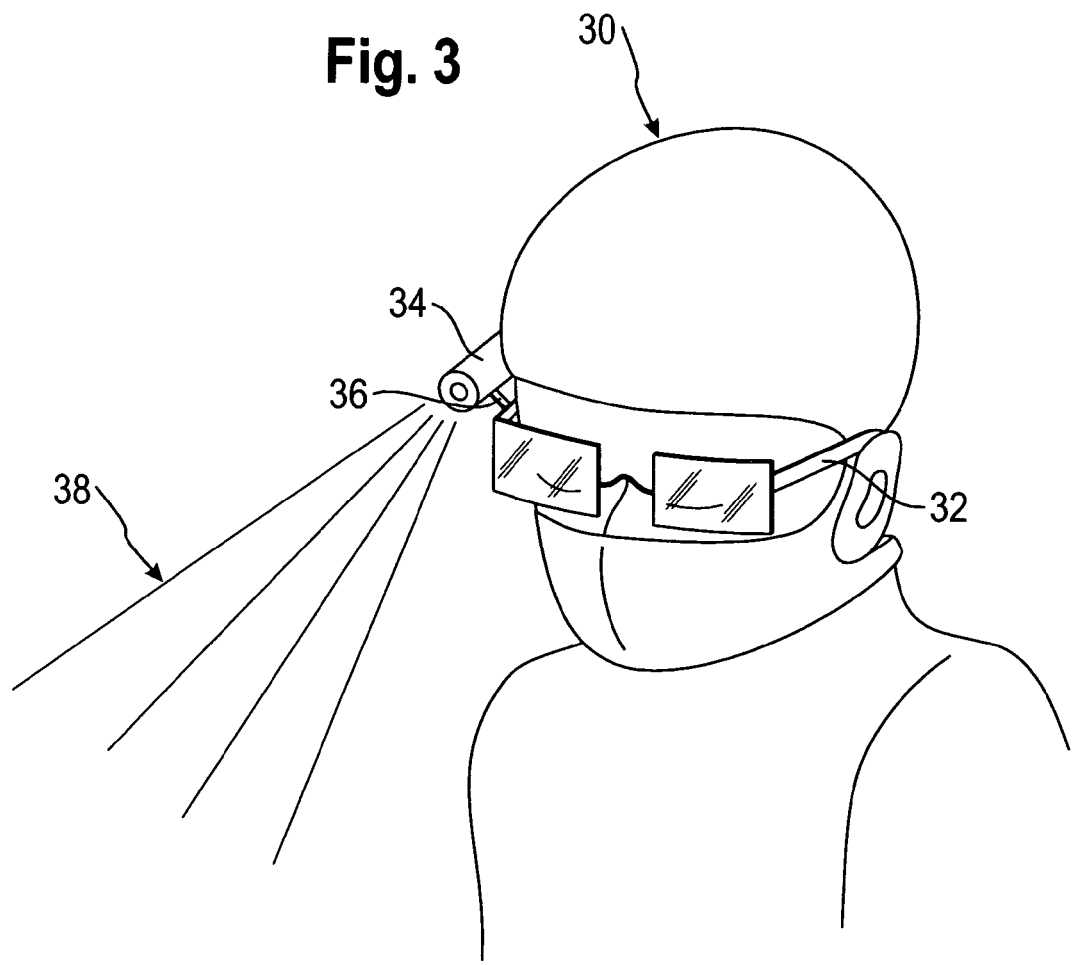

INTEGRATED SURGICAL DEVICE COMBINING INSTRUMENT, TRACKING SYSTEM AND NAVIGATION SYSTEM

This application is a national phase of International Application No. PCT/EP2009/060760 filed Aug. 20, 2009 and published in the English language.

The present invention relates to an image guided surgery system and, in particular, an integrated surgical device combining an instrument, a tracking system and a medical navigation system.

Image guided surgery systems and elements thereof are known in general, for example, from DE 196 39 615 A1; U.S. Pat. No. 5,389,101 or U.S. Pat. No. 6,978,167 B2 which documents in particular describe navigation systems which form an essential part of an image guided surgery system.

As its main components, an image guided surgery system according to the present invention comprises a surgical instrument; a tracking system for locating and tracking an object in a surgical environment, the tracking system including a tracking sensor system, in particular a camera system; and a medical navigation system processing tracking data from the tracking system and image data of the object, and outputting image data and navigational assistance on a display. The display is a part of the image guided surgery system but may also be regarded as an element of the navigation system. The data and image processing as performed by the tracking system and the medical navigation system is corrected out on a computerized basis including a CPU and memory means as well as data transfer means.

Known image guided surgery systems such as the ones mentioned above feature their elements in the form of relatively large, separate devices, namely a separate surgical instrument or a set of surgical instruments which may comprise markers or marker arrays for tracking purposes; a camera unit (with two cameras) and, in some instances, a light transmitter, said camera unit being used as a tracking system; and a computer unit serving as a data processor of a navigation system, which computing unit is connected to a display, for example, a computer screen.

Disadvantageously, the components of known image guided surgery systems take up a large amount of space in an operating theater, and they need to be arranged in a special manner for each operation. In this respect, it must be provided for free lines-of-sight to ensure proper functioning of the tracking system and, on the other hand, all of the devices must be arranged in such a way that they do not disturb the surgeons and their assistants during their work. Moreover, surgeons must frequently turn their view away from the field of operation in order to take a look at the monitor or computer screen for navigational assistance.

It is the object of the present invention to provide an image guided surgery system overcoming at least some of the above-mentioned disadvantages. In particular, the invention has been made with a view to providing an easy-to-handle system, both regarding set-up and use.

To this end, the present invention provides an image guided surgery system according to claim 1. The sub-claims define advantageous embodiments of the invention.

In one aspect of the present invention, the system is designed in such a way that the instrument, the tracking system including the sensor system and the medical navigation system including the display are integrated in one single portable unit. In other words, the invention provides all of the essential elements of an image guided surgery system in a one-part form which can easily be manipulated by a user.

In making the invention, it has been realized that such essential elements may be provided in a miniaturized and light-weight embodiment and be put together in the form of one single unit, this approach simultaneously solving more than one problem of the prior art. Namely, there are no longer any set-up-problems because one single integrated system does not require a setting-up of its elements. Moreover, since the instrument is a part of the inventive one-unit system the entire system will, at any point of time, be in the region of interest, namely where the instrument is used in the field of operation, so that a surgeon must not turn his attention away from the region of interest in order to take a look at the display showing the navigational assistance. This is because the display forms just another integrated part of the system and is thus located where the instrument in use is located. Other advantages include the fact that such image guided surgery systems which are provided as small, portable devices may readily be used and transferred between operating theaters with hardly any effort.

The single portable unit may be a hand-held device, in particular a device to be held in one hand by a surgeon or a medical assistant. The respective design will much depend on the instrument used. Many instruments which are manipulated with one hand may be part of the inventive image guided surgery system, such as pointers, forceps, catheters or scalpels etc. On the other hand, any instruments which may be navigated are apt to be used with the system according to the present invention, for example, drills, drill guides or bone cutting block adapters etc.

In order to provide stereoscopic tracking, the tracking sensor may be a two-camera system. However, it is possible to realize the present invention by using one single tracking sensor, in particular one single tracking camera. In general, the tracking system may be an optical tracking system using cameras or one camera, but it may also be an electromagnetic or magnetic tracking system as well as an ultrasound or sound tracking system.

In one embodiment of the image guided surgery system, the tracking camera is a video camera, namely a camera continuously capturing images or capturing subsequent discrete images over a certain period of time. The term "video camera" means a camera operating with light in the visible part of the light spectrum in contrast to, for example, an infrared camera which may also be used but is less preferred. The use of such a video camera is highly advantageous because said cameras are available on the market in miniaturized embodiments as relatively inexpensive mass products. The use of such a video camera thus reduces the overall costs of an image guided surgery system.

The single unit system of the invention may comprise a housing accommodating the navigation system and the display. The tracking sensor system, in particular the tracking camera system may be arranged anywhere on the housing for appropriate imaging, in particular on the side opposed to the display so that the display can be kept in view by the surgeon on one side of the system unit, while sensor images the field of operation.

The instrument may be rigidly and positionally determined attached or attachable to the housing, in particular by means of an instrument adapter. Such an instrument adapter may also comprise an electronic identification device cooperating with a respective device on the instrument so that—upon mounting the instrument—the navigation system will immediately be informed of the type and characteristics of the instrument.

In another embodiment of the image guided surgery system, the tracking system or the navigation system comprise logic which deduces positional information about the object form images made in different or separate tracking sensor positions, in particular form images made subsequently or continuously with a moving sensor. In this way, for example, information taken with one single video camera, i.e. two-dimensional information, may be upgraded in such a way that enough data about the spatial position of the object is retrieved, such that navigational systems can be provided. Other ways of providing more spatial information include the use of a touch-free distance sensor or a time-of-flight camera supplementing or replacing the tracking sensor, thereby collecting information about a distance between the object and the unit or a depth of the object or of one its elements. A time-of-flight camera is a camera system that creates distance data with the help of the time-of-flight principle. The scene is illuminated by short light pulses and the camera measures the time taken until the reflections reach the camera again. This time is directly proportional to the distance. The camera therefore provides a range value for each imaged pixel. The principle is similar to that of 3D-scanners with the advantage that a whole scene is captured at the same time.

One further way of making-up or compensating for reduced tracking accuracy comprises equipping the instrument can with adjustment means for setting a determinable or predetermined positional relationship between the unit and the object or elements attached to the object.

When integrating the display, the tracking system and the instrument into a single unit, a small portable "all-in-one" navigation system is created. All the system needs to do is to figure out where it is located with respect to an object reference, and in this way, a tracking of the instrument can be eliminated since there is a fixed relationship between the instrument and the tracking system. In other words, the transition matrix from the tracking system (camera) coordinates to instrument coordinates does not change because both elements are integrated in one piece of hardware.

As the tracking system or tracking camera will automatically always be in or near to the field of operation, there are hardly any visibility problems or line-of-sight problems. Since the video image from the tracking system camera may be displayed "live", i.e. in real time, on the system's display, it is very easy to aim the camera at a target, for example, at a reference array attached to the object (for example a bone).

In accordance with another aspect of the present invention, an image guided surgery system is provided which comprises
 a surgical instrument,
 a tracking system for locating and tracking an object in a surgical environment, the tracking system including a tracking sensor system, in particular a tracking camera system; and
 a medical navigation system processing tracking data from the tracking system and image data of the object, and outputting image data and navigational assistance on a display.

The instrument and the medical navigation system including the display are integrated in one single portable unit, while at least the sensor system of the tracking system is arranged at a location near a region of interest determined by the object and the field of surgery.

The sensor system may be arranged at a location which is spaced from the region of interest by a distance which is not exceeding five times the longest dimension in the region of interest, in particular in the field of surgery. In another embodiment, the distance will not exceed two times the longest dimension in the region of interest. The term "longest dimension" may, for example, mean that if the area in which the actual operation takes place, that is where the instruments are used is approximately circular, the longest dimension is the diameter of such a "circle". In a rectangular field of operation, said "longest distance" may be the diagonal of the rectangle.

The sensor system may, in accordance with one embodiment of this aspect of the invention, be mounted on a device to be worn or attached to a surgeon's head, in particular on a surgeon's head band, surgeon's eyeglasses or a surgeon's head lamp; or on said unit.

Figure 2:
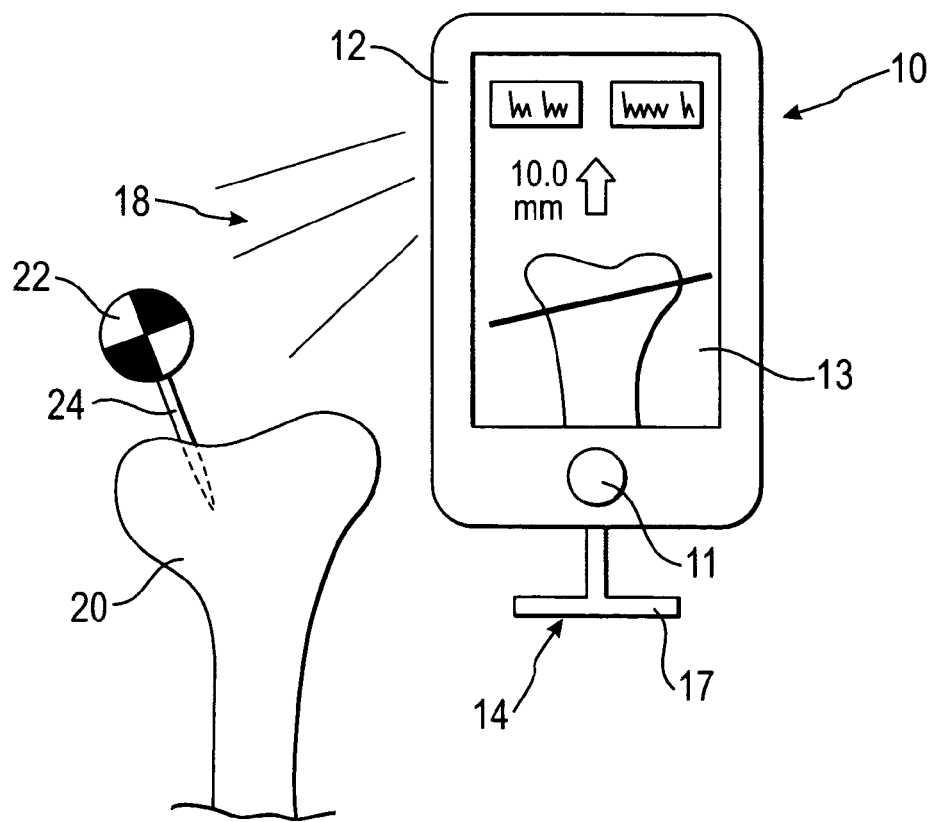

The invention will now be described in more detail by referring to particular embodiments and to the attached drawings. It is to be noted that each of the features of the present invention as referred to herein may be implemented separately or in any expedient combination. In the drawings:

FIGS. 1 and 2 show a single-unit image guided surgery system in accordance with one embodiment of the present invention in use and from different viewing angles, and FIG. 3 shows a tracking sensor arrangement in accordance with one aspect of the present invention.

FIG. 1 shows a single-unit image guided surgery system 10 presently imaging an object 20, namely a bone, on which a tracking marker 22 is fixed by a mounting device 24. FIG. 2 shows the same situation from a different angle of view, namely from a view onto the front side of the system 10, with the bone 20 being arranged behind the system 10.

The system comprises a housing 12 which has, on its front side, a display 13 and an input button 11. The display 13 may be a touch-sensitive display so that it can be used for input purposes, too. The system 10 further comprises an instrument 14 which is fixedly attached to the housing 12 by means of an adapter (not shown). In the present example, the instrument 14 has a simple configuration with a lower elongated or flat portion 17 of known positional relationship to the housing and to a single video camera 16 placed on the back side of said housing 12. By means of the flat or elongated, straight portion 17 of the instrument 14, it is, for example, possible to detect the position or orientation of a flat or straight portion of an object in relation to a reference array or reference means (for example marker 22) arranged on said object (for example bone 20).

The object in question is located in the field of view 18 of the camera 16. The positional information which can be gathered because the system 10 is a single unit, is processed together with image data by a navigation system 15 accommodated in the housing 12. The result of the data processing of the navigation system is then shown on display 13 as combined and related image data and positional data, in other words as navigational assistance.

The navigation system itself is, in particular, merely a computerized system, i.e. a data processing system for processing image data and position data supplied by the tracking system, namely the video camera 16. In this respect, the navigation system may be provided in the housing as a separate data processing system with all necessary elements (data transfer means, CPU, data storage means, memory). On the other hand, such data processing may also be required in extracting positional data (x-, y-, z-coordinates) from the images made by camera 16. Such data processing for the tracking system may be provided at a separate data processing system, although it is possible and may be advantageous to use one single data processing system for processing tracking data and for providing navigational data processing. In this respect, the dashed unit 15 in FIG. 1 might also be a single data processing unit having tracking and navigation purposes and supplying graphical support to show navigational assistance on the display 13.

The "all-in-one" image guided surgery system 10 may thus, on the one hand, detect positional information regarding the positional relationship between the system and its instrument and an object (bone), and, on the other hand, serve to display navigational information, i.e. positional information combined with image data (as shown on the display 13 in FIG. 2).

An example for placing a tracking system near to a region of interest is shown in FIG. 3. The "region of interest" is determined by an object in a surgical environment and the field of surgery and said region of interest may coincide with the field of operation in which a surgeon works. FIG. 3 shows the head of a surgeon 30 wearing surgeon's eyeglasses 32. Fixed with an adapter 36 to the eyeglasses 32 is a single light-weight video camera 34, for example a miniaturized mass-product camera having a field of view 38. With such an arrangement, the camera is mounted near the region of interest, the head of the surgeon will be directed to and in the very vicinity of said region. Moreover, any problem with an interrupted line-of-sight can be eliminated, since the camera will always be directed onto the region of interest together with the view of the surgeon.

Of course, other embodiments are possible, such as cameras mounted on the instrument used by the surgeon or the display used by the surgeon. In accordance with this or any aspect of the invention other tracking technologies may be used, like electromagnetic, ultrasound, IR-light-camera tracking or visible-light camera tracking.

It has been mentioned above that—according to one embodiment of the invention—inexpensive mass-product video cameras may be used for tracking purposes. Under certain circumstances, these cameras may not be able to achieve a very high three-dimensional accuracy for tracking points in space. On one hand, these problems may be made up for by using special techniques, for example, color-coded markers. On the other hand, the system may still be featuring enough accuracy for a couple of important applications, since in some of these applications, the main interest does not reside in exactly locating points in space. One example herefore might be navigating a cutting plane on a bone.

It is possible to base the function of the inventive system merely on the use of two-dimensional information. Theoretically, when using one single camera, one just needs to have enough markers to determine accurate three-dimensional positions from two-dimensional information. However, a certain number of tasks might not require full-3D information and the camera merely has to be positioned in such a way that the "interesting information" may be deduced from two-dimensional camera movement. One example might be looking with one single camera at the knee from the front. In this instance, the varus-valgus angle of a tool may be determined without knowing its exact depth. One may also use markers which can be directly attached to the bone, for example, adhesive markers.

Hardware support may also be taken into consideration when trying to compensate for reduced tracking accuracy. For instance, hardware components may be used which split-up the degrees of freedom of a given tool, like a fine adjustable cutting block adapter which uses turning wheels to separately adjust three degrees of freedom. Then, navigation can be split up into different steps, the camera always being pointed in the "right" direction for any specific step.

Should there, however, actually exit a need for adding depth information, i.e. information about the actual distance between the inventive system or its camera and the object, there are further possibilities like using a distance sensor or a time-of-flight camera as has already been mentioned and explained in greater detail above.

The invention claimed is:

1. An image guided surgery system, comprising:
a surgical instrument comprising a flat or elongated portion;
a tracking system configured to locate and track an associated object having a flat or straight portion in a surgical environment, the tracking system comprising a tracking camera system configured to track a reference array or reference marker arranged on the associated object, the tracking system being further configured to provide tracking data and image data of the associated object; and
a medical navigation system comprising a computer, the medical navigation system configured to process the tracking data and the image data of the associated object, and to output the processed image data of the associated object and positional information based on the processed tracking data on a display,
wherein the surgical instrument, the tracking system including the tracking camera system, and the medical navigation system including the display are integrated in one single portable unit comprising a generally rectangular housing accommodating the medical navigation system and the display, the surgical instrument being rigidly attached or attachable to the housing in a known position relative to the housing, wherein the flat or elongated portion of the surgical instrument extends in a direction substantially transverse to the generally rectangular housing,
wherein the flat or elongated portion of the surgical instrument is of a known positional relationship relative to the housing, in order to detect an orientation of the flat or straight portion of the associated object relative to the reference array or reference marker.

2. The system according to claim 1, wherein the one single portable unit is a hand-held device.

3. The system according to claim 1, wherein the tracking camera system has only one single tracking camera.

4. The system according to claim 1, wherein the tracking camera system is arranged on the housing.

5. The system according to claim 4, wherein the tracking camera system is arranged on a side of the housing opposite the display.

6. The system according to claim 1, wherein one or more of the tracking system and/or the medical navigation system comprise logic which when executed by a processor of the system is configured to deduce positional information corresponding to the associated object from images made in different or separate tracking camera positions.

7. The system according to claim 1, wherein the surgical instrument comprises an adjustment device configured to set a determinable or predetermined positional relationship between the one single portable unit and the associated object or the reference array or reference marker arranged on the associated object.

8. The system of claim 1, wherein the one single portable unit includes comprises at least one of a touch-free distance sensor or a time-of-flight camera.

9. The system according to claim 1, wherein:
the surgical instrument of the image guided surgery system defines a set of surgical instrument coordinates;
the tracking system of the image guided surgery system defines a set of tracking system coordinates; and the medical navigation system is configured to process the tracking data and the image data of the associated object, and to output navigational assistance on the display, using a fixed transition matrix relating the set of surgical instrument coordinates of the surgical instrument with the set of tracking system coordinates of the tracking system.

10. An image guided surgery system, comprising:

a surgical instrument;

a tracking system configured to locate and track an associated object having a flat or straight portion in a surgical environment, the tracking system comprising a tracking camera system operable to track a reference array or reference marker arranged on the associated object, the tracking system being further configured to provide tracking data and image data of the associated object; and a medical navigation system comprising a computer and a display, the medical navigation system being configured to process the tracking data and the image data of the associated object, and to output the processed image data and navigational assistance on the display, the navigational assistance comprising positional information based on the processed tracking data, wherein the surgical instrument, the tracking system including the tracking camera system, and the medical navigation system comprising the computer and the display are integrated in one single portable unit comprising a generally rectangular housing accommodating the navigation system and the display, wherein the instrument is rigidly attached or attachable with the housing in a known position relative to the housing, wherein the surgical instrument comprises a flat or elongated portion extending in a direction substantially transverse to the generally rectangular housing, wherein the flat or elongated portion of the surgical instrument is of known positional relationship to the housing, in order to detect an orientation of a flat or straight portion of the associated object in relation to the reference array or reference marker.

11. The system according to claim 10, further comprising a video camera configured to be worn or attached to a surgeon's head by an associated mounting device.

12. The system according to claim 11, wherein the associated mounting device comprises at least one of a head band, eyeglasses or a head lamp.

13. The system according to claim 10, wherein the tracking camera system is a single tracking camera.

14. The system according to claim 10, wherein the tracking camera system comprises a video camera.

15. The system according to claim 10, wherein:

the surgical instrument of the image guided surgery system defines a set of surgical instrument coordinates;

the tracking system of the image guided surgery system defines a set of tracking system coordinates; and the medical navigation system is configured to process the tracking data and the image data of the associated object, and to output the navigational assistance on the display, using a fixed transition matrix relating the set of surgical instrument coordinates of the surgical instrument with the set of tracking system coordinates of the tracking system.

\* \* \* \* \*